United States Patent [19]

Katsura et al.

[11] Patent Number: 4,499,054
[45] Date of Patent: Feb. 12, 1985

[54] CATION EMISSION TYPE HALOGENATED HYDROCARBON GAS DETECTING ELEMENT

[75] Inventors: Masaki Katsura, Yokosuka; Mituo Harata, Kawasaki; Osamu Takikawa, Kamakura; Masayuki Shiratori, Kawasaki, all of Japan

[73] Assignee: Tokyo Shibaura Denki Kabushiki Kaisha, Kawasaki, Japan

[21] Appl. No.: 411,019

[22] Filed: Aug. 24, 1982

[30] Foreign Application Priority Data

Aug. 31, 1981 [JP] Japan .................. 56-135414

[51] Int. Cl.³ ............................. G01N 27/62
[52] U.S. Cl. ..................... 422/98; 324/468; 436/126; 436/153
[58] Field of Search .......... 422/98; 436/126, 149, 436/153; 73/23; 204/425, 1 B; 338/34; 324/468, 469

[56] References Cited

U.S. PATENT DOCUMENTS

| 2,742,585 | 4/1956 | Zemany | 324/468 X |
| 2,806,991 | 9/1957 | White | 324/468 |
| 3,882,012 | 5/1975 | Dickinson et al. | 204/195 P |
| 3,972,480 | 8/1976 | Powers | 241/15 |
| 4,166,009 | 8/1979 | Fray | 204/1 T |

FOREIGN PATENT DOCUMENTS

| 7516931 | 2/1976 | Fed. Rep. of Germany . |
| 2426905 | 12/1979 | France . |
| 1603496 | 11/1981 | United Kingdom . |

OTHER PUBLICATIONS

Choudhary et al., Solid Electrolytes and Their Applications, 1980, pp. 49-57.
"Electronics Simulates Sense of Smell," Electronics, Mar. 1948, pp. 100-102.

Primary Examiner—Michael S. Marcus
Assistant Examiner—Michael S. Gzybowski
Attorney, Agent, or Firm—Schwartz, Jeffery, Schwaab, Mack, Blumenthal & Koch

[57] ABSTRACT

A cation emission type halogenated hydrocarbon gas detecting element comprising a cation source, a heating means and an ion collector electrode, which is characterized in that said cation source consist essentially of $\beta$-$Al_2O_3$, wherein substantially all cation species occupy a position in the crystal lattice structure of the source. By employing $\beta$-$Al_2O_3$, the detecting element can be more miniaturized and can work at lower temperature than a conventional cation emission type electrode comprising the cation source made of steatite.

2 Claims, 1 Drawing Figure

CATION EMISSION TYPE HALOGENATED HYDROCARBON GAS DETECTING ELEMENT

BACKGROUND OF THE INVENTION

This invention relates to a halogenated hydrocarbon gas detecting element of cation emission type.

Halogenated hydrocarbon gas has been widely used as refrigerant gas or coolant for electric refrigerators, air conditioners and the like. Halogenated hydrocarbon has a chemical formula wherein one or more of the hydrogen atoms has been replaced by chlorine, fluorine or the like, and typically includes R-12 ($CCl_2F_2$), R-22($CHClF_2$), etc. These halogenated hydrocarbons are chemically and thermally very stable, harmless to human bodies, and have excellent thermodynamical characteristics when they are used for refrigeration systems.

In the refrigeration systems, the halogenated hydrocarbon gas mentioned above is alternately compressed and expanded to cause its refrigeration actions. A this time, a trace amount of the halogenated hydrocarbon gas may sometimes leak away from compressors, radiators, pipes, etc. If such leaks are left unstopped, efficiency of the refrigeration systems is lowered due to a gradual decrease of the refrigerant gas, with the result of a possible stop of the function of such equipments. Accordingly, severe control is required when such equipments are manufactured in a factory, and it is desirable to periodically check any leak along the pipe systems. Especially, in the refrigeration systems such as air conditioners for cars and the like, there is a greater possibility of leak due to a shock during drive, and a detector which may simply find out the leaks has long been desired.

Generally, the air conditioner as mentioned above is heavy in weight, and in addition it is usually fixed at one place or mounted on a car. Therefore, it is impossible to make an inspections thereof by simply turning or overturning it. Moreover, the leaks are usually too small to find out visually or by a magnifier. Further, it is desirable for an element for detecting leaks to be as miniature as possible since the pipe system, etc. is usually of complicated structure. Still further, the detecting end of an element should preferably be as small as possible in diameter since the detecting element traces the pipe or the like to locate a leak. In addition, it is required that a detecting element can be operated by means of a miniature cell or cells in order to make it easy to handle. While the sensitivity of a detector is desirably as high as possible as a matter of course, it is required for it to detect a gas leak of at least $10^{-4}$ cc/sec (25° C., 1 atm).

There has been proposed a number of halogenated hydrocarbon gas detectors, some of examples of which are being explained below:

A typical detector, a torch, utilizes a kind of flame reaction; it utilizes the phenomenon that the color of flame changes responding to the chemical reaction of the halogen gas mixed into the flame with a copper metal provided in the flame. Although this method is simple, it is often accompanied by errors because the presence or absence of leaks is visually judged. Moreover, the limit of detection according to this method is $10^{-2}$ cc/sec (25° C., 1 atm) at best.

Further, there has been proposed a detector which utilizes high voltage electric discharge. This detector is provided with a pair of electrodes exposed to air with a gap therebetween, to which electrodes is applied a high voltage of several hundred volts for producing an electric discharge at the gap. The discharge stops when halogenated hydrocarbon gas comes into the gap between the electrodes. As a result, the leak can be detected by detecting the change of the discharged current, with the detection limit leveled up to $10^{-3}$ cc/sec (25° C., 1 atm) which is sufficient for practical use. However, this detector, which utilizes the electric discharge, is disadvantageous in for example that the discharge is interrupted due to other external causes such as wind or the like even when there is no leak of the halogenated hydrocarbon gases.

On the other hand, as a detector having sufficiently high sensitivity, there has been known a detector called a cation emission type leak detector. The detector of this type comprises ceramics such as steatite containing Na, K, etc., an ion collector electrode and a heater. The ceramics are heated to a high temperature (e.g. 800° C.), to which ceramics there is provided at a predetermined space an ion collector electrode made of a metal. While a high voltage of about 300 V is applied to the space between the ceramics and the ion collector electrode, the halogenated hydrocarbon gas is reacted on the surface of the ceramics due to the high temperature to emit ions of Na, K, etc. contained in the ceramics, which ions are attracted to and captured by the metallic electrode with the aid of the high voltage. As the result, the leak can be detected by detecting ionic current thus generated. According to this detector, the detection limit is not more than $10^{-6}$ cc/sec (25° C., 1 atm) and thus the detector exhibits very high sensitivity.

However, the detector of this type consumes the electric power of as large as 20~30 W because the ceramics must be kept at a high temperature (about 800° C.) as mentioned above, whereby not only a larger size of an apparatus but also a cord for the power source are required. Moreover, when the detector of this type is in contact with an unexpectedly high concentration of the halogenated hydrocarbon gas, the alkaline metals in the vicinity of the surface of the ceramics such as the steatite mentioned above are ionized in large quantitites to form a flow of cations which flows to a cathode undesirably, with the result that the alkaline ions in the vicinity of the surface of said ceramics have been consumed. Accordingly, because of paucity of alkaline ions on the surface of the ceramics, a quick response of the detector can not be expected even if it is brought again into contact with halogenated hydrocarbon gas, and the sufficient detecting sensitivity can not be obtained until the alkaline ions in the ceramics are recovered by having diffused sufficiently in the vicinity of the surface. It is therefore necessary for the ceramics to be heated at a high temperature so that the alkaline ions may readily migrate from the inside of the ceramics to the surface thereof. It is for this reason that the temperature of the element must be kept at 800° C. as aforementioned, but nonetheless it shows unavoidable non-sensitivity during a time of several to several ten minutes after having detected halogenated hydrocarbon gas of a high concentration. Such a high temperature further causes disadvantageously a serious breakage or wear of the metallic electrode, and especially a short life time of a heating wire serving also as an anode. In addition, the detector of this type, which detects the halogenated hydrocarbon gas while consuming the alkaline ions which are finite, has necessarily a limited life time since the whole quantity of the alkaline metal ions contained in the aforesaid ceramics is extremely small.

SUMMARY OF THE INVENTION

In view of the drawbacks in the conventional detecting elements as mentioned above, this invention aims to eliminate them and to provide a cation emission type halogenated hydrocarbon gas detecting element which consumes less electric power, and is of a low price and a high efficiency.

According to this invention, the cation emission type halogenated hydrocarbon gas detecting element comprises a cation source, a heating means and an ion collector electrode, and is characterized in that a beta-alumina ($\beta$-$Al_2O_3$) is used as said cation source.

DETAILED DESCRIPTION OF PREFERRED EMBODIMENTS

Figure 1:
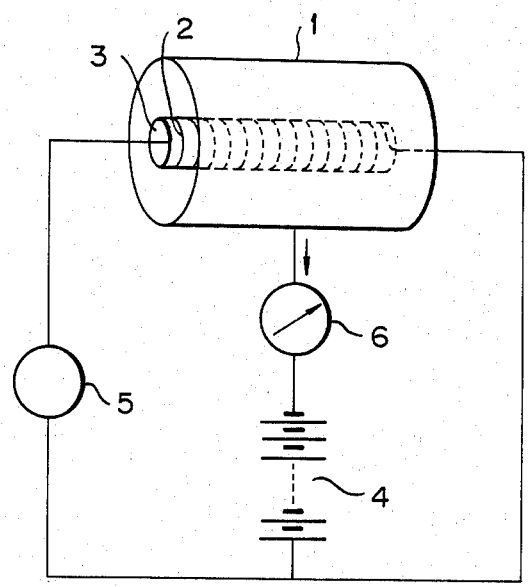

By employing $\beta$-$Al_2O_3$, which is well known to be a solid electrolyte, in place of the steatite conventionally used as the cation source, it becomes possible to miniturize the size of the element to a great extent, and improve the durability of the element as it can work at a lower temperature. Furthermore, according to this invention, it is unnecessary to limit the material for ion collector electrode used as an opposite pole to a particular material such as platinum which has been required in the conventional detector, and it is possible to use an ordinary material such as Ni.

Beta-alumina($\beta$-$Al_2O_3$) to be used in this invention is commercially available or may be prepared by a conventional method, e.g., in the following manner:

Powders of alpha-alumina($\alpha$-$Al_2O_3$) and sodium monoxide ($Na_2O$) or sodium hydrogencarbonate($NaHCO_3$) are mixed in predetermined amounts and calcined at 1250° C., to which is added an organic binder such as a 2 wt % solution of PVA. A mixture thus obtained is pressed under pressure of 1 ton/cm$^2$, followed by removing the organic solvent at 800° C. in air and firing the resultant product at 1600° to 1700° C. for two hours in a Pt or MgO crucible, thereby obtaining a beta-alumina($\beta$-$Al_2O_3$).

This invention will be described below in more detail by giving examples of its embodiments and comparing them with a conventional detector, with reference to the accompanying drawing (FIG. 1):

EXAMPLE 1

FIG. 1 illustrates a basic construction of a halogenated hydrocarbon gas detecting element of cation emission type. For comparison, prepared was a conventional cation emission type halogenated hydrocarbon gas detecting element having such a basic construction as shown in FIG. 1. In FIG. 1, reference numeral 1 denotes an ion collector electrode made of platinum of a cylindrical shape, numeral 2 a heater for heating ceramics containing alkaline ions, and numeral 3 the ceramics as a cation source, i.e. steatite, containing the alkaline ions; these are the basic components constituting the detecting element. A measuring circuit is also shown together in FIG. 1 by illustrating its principle; numeral 4 denotes a high voltage electric source which forms direct current electric field at the space between the ion collector electrode 1 and the heater 2, charging the former with negative and the latter with positive. Numeral 5 denotes an electric source for heating, which may be of either alternating current or direct current. Numeral 6 denotes an ampere meter for measuring the ionic current which corresponds to the quantity of halogenated hydrocarbon gas.

Also prepared was a cation emission type halogenated hydrocarbon gas detecting element according to the invention, which has substantially the same basic construction as shown in FIG. 1 and provided with $\beta$-$Al_2O_3$ as the cation source 3 in place of steatite in the conventional detecting element. The $\beta$-$Al_2O_3$ employed was the one available from Toshiba Ceramics Co., Ltd. and having composition of 1.2 $Na_2O.11$ $Al_2O_3$ containing 6.2 wt % of Na. Comparing the efficiency of the detecting element of this invention with that of the abovementioned conventional one, the results were as follows:

In the case of the conventional detecting element, which was provided as the cation source 3 in FIG. 1 with the ceramics of steatite containing alkaline ions, it was necessary to heat said steatite to 800° C. or higher in order to promote emission of a sufficient quantity of the alkaline ions.

In contrast thereto, the $\beta$-$Al_2O_3$ used in this invention, having in nature relatively higher mobility of $Na^+$ ions even at a room temperature, showed enhanced mobility of the $Na^+$ ions. Accordingly, having constructed such detecting element as shown in FIG. 1 by using the $\beta$-$Al_2O_3$, a lower temperature of about 300°~600° C. was employable as a matter of fact.

Since the ionic concentration of the alkaline ions present at the surface of the $\beta$-$Al_2O_3$ solid electrolyte of this invention is higher than that of the conventional steatite, the cation source which is smaller in size than the conventional one, i.e. the one smaller in the surface area of the cylindrical body corresponding to the numeral 3 in FIG. 1, was sufficiently suited to a practical use; in fact, $\beta$-$Al_2O_3$ having the surface area which was smaller by a factor of about 1/10 was operable as the cation source of the detecting element. Therefore, the detecting element according to this invention was able to be miniturized to about ⅓ size by employing the $\beta$-$Al_2O_3$. In addition thereto, the electric power to be consumed by the heater 2 was as small as not more than 1/10 of the power consumed by the conventional detecting element, because it was possible for the detecting element of this invention to work at the aforementioned lower temperature.

The detecting element of this invention was further advantageous in that it was not the case with the invention that the element had no sensitivity for a long time as in the case of the conventional type after it came into contact with the gas of a high concentration, because the migration of $Na^+$ ions in the $\beta$-$Al_2O_3$ was performed swiftly; the sensitivity of the detector of this invention was recovered in about five seconds even after it was exposed to a 100% concentration of the halogenated hydrocarbon gas for about ten seconds.

EXAMPLE 2

Prepared was a detecting element according to this invention in the same manner as in Example 1 except that the ion collector electrode made of platinum was replaced by one made of nickel to compare its performance with that of the conventional detecting element. Substantially the same results as in the case of Example 1 were obtained.

As described in the foregoing, the conventional detecting element, whose temperature reaches as high as 800° C., employs platinum or the like as the material for the ion collector electrode because otherwise it seriously shows change in its characteristics or is damaged by the oxidation of the heating wire and the collector electrode. However, it is well known that the platinum is limited in resource and high in price, so that the price of the detecting element has been raised, and there has been a problem in using it widely.

Whereas, for the detecting element according to this invention, ordinary metals including Ni and the like can be used with substantially no problem because of its lower operating temperature. Besides, since it can be miniturized, wide use thereof can be expected. Further, it becomes feasible that the element is operable with cells because the electric power to be consumed by it is as small as 2 to 3 W, and therefore it has become possible to provide a detector which is easy to use even at a place distant from an electric source or at a complicated place, while the conventional detector has required an electric source of AC 100 V. These advantages result from the employment of $\beta$-$Al_2O_3$ as the alkaline ionic source. As a result, there can be provided a detector which is not only superior in the detecting efficiency to that of the conventional detector, but also very easy to handle practically.

What is claimed is:

1. In a cation emission type halogenated hydrocarbon gas detecting element comprising a cation source, a heating means and an ion collector electrode, the improvement wherein said cation source consists essentially of Beta-$Al_2O_3$, wherein substantially all cation species present in said cation source occupy positions in the crystal lattice structure of said Beta-$Al_2O_3$.

2. The detecting element according to claim 1, wherein said ion collector electrode is made of nickel.

* * * * *